United States Patent [19]

Pfirrmann

[11] Patent Number: 4,604,391

[45] Date of Patent: Aug. 5, 1986

[54] TREATMENT OF OSTEITIS AND OSTEOMYELITIS EMPLOYING THIADIAZINE COMPOUNDS

[75] Inventor: Rolf W. Pfirrmann, Lucerne, Switzerland

[73] Assignee: Ed Geistlich Sohne AG fur Chemische Industrie, Switzerland

[21] Appl. No.: 662,885

[22] Filed: Oct. 19, 1984

[30] Foreign Application Priority Data

Oct. 20, 1983 [GB] United Kingdom ............... 8328073

[51] Int. Cl.$^4$ .............................................. A61K 31/54
[52] U.S. Cl. ............................................... 514/222
[58] Field of Search ....................................... 514/222

[56] References Cited

U.S. PATENT DOCUMENTS 4,107,305 8/1978 Pfirrmann ........................ 514/222
4,337,251 6/1982 Pfirrmann ........................ 514/222

FOREIGN PATENT DOCUMENTS 1124285 8/1968 United Kingdom .

*Primary Examiner*—Allen J. Robinson
*Attorney, Agent, or Firm*—Bernard, Rothwell & Brown

[57] ABSTRACT

Compounds of formula (I)

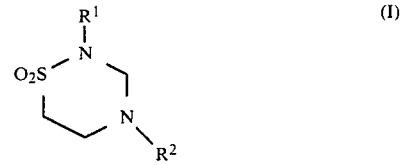

[wherein $R^1$ represents a hydrogen atom or an alkyl group having from 1 to 6 carbon atoms and $R^2$ represents a hydrogen atom, an alkyl group having from 1 to 6 carbon atoms or a group of formula (II)

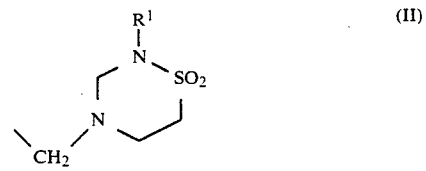

in which $R^1$ is as defined above] and pharmaceutical compositions thereof may be administered prophylactically to humans or warm-blooded animals to combat the occurrence of osteitis or osteomyelitis, especially in patients suffering from bone injuries of traumatic origin.

4 Claims, No Drawings

TREATMENT OF OSTEITIS AND OSTEOMYELITIS EMPLOYING THIADIAZINE COMPOUNDS

This invention relates to compositions for use in prophylactic treatment against osteitis and osteomyelitis.

In spite of intensive research both in the clinic and the laboratory, osteitis, that is bone infection following injury or surgery, remains a feared complication in traumatology and orthopaedics. Although antibiotics can be helpful, they cannot be relied upon for certain to prevent or heal osteitis, whether given therapeutically or prophylactically (G. Hierholzer and G. Lob "Antibiotikatherapie in der Unfallchirurgie" Unfallchir. 81,64 (1978); D. Stolle et al "Antibioticaprophylaxe in der Traumatologie" Hefte Unfallheilk. 143 (1980); G. Lob and C. Burri "Perioperative Infektionsprophylaxe mit Antibiotika oder Disinfektionsmitteln" page 157 ff in 2. Saarbruecker Gespraeche, P. Eckert Ed., Zucksch-werdt, Munich 1982).

A case of acute post-traumatic osteitis may be succesfully treated by immediate specific therapy, but acute osteitis often proceeds into a chronic, therapy-resistant stage. Chronic post-traumatic osteitis may at any time, even after many years, flare up and become active once again so that, at most, it is possible to speak of "a state of suspended activity" in a case of osteitis. It is not possible, by definition, to speak of a "cure" in chronic post-traumatic osteitis (C. Kaufmann "Handbuch der Unfallmedizin" Enke, Stuttgart 1925; C. Burri "Posttraumatische Osteitis" 2nd Edition, Huber, Bern/Stuttgart/Vienna, 1979; I. Schweiberer "Verheutung und Behandlung von Infektionen nach Osteosynthesen" Chirurg. 48, 1 (1977)).

Similarly osteomyelitis, which is a bone infection of haematogenous origin, is extremely difficult to cure by conventional methods. It seems possible that osteomyelitis does, in fact, arise from traumatic incidents such as cracked bones which may not be thought serious at the time (Morrissy et al, 26th Annual ORS, Atlanta, Georgia, 1980).

In the treatment of osteitis and osteomyelitis, necrotic bone (sequester) is normally rigorously removed since it has been found to promote the return of the disease even after antibiotic treatment. The mechanism of this reactivation has not hitherto been clear but we have now established that such necrotic bone contains a very high concentration e.g. up to about 5%, of bacterial toxins, including both endotoxins of lipopolysaccharide character and exotoxins which are essentially proteins. The infected site also contains bacteria but it has not previously been recognised that large toxin concentrations were present. Bacteria and their toxins found to be present in such infected bone include aerobic bacteria such as Staphylococcus, Klebsiella, Proteus, Pseudomonas, Escherichia, and Citrobacter as well as anaerobic bacteria such as Peptococcus, Streptococcus Enterococcus, Peptostreptococcus, Veillonella, Bacteroides, Fusobacterium, Clostridium, Propionibacterium and Eubacterium.

We have further established that cetain methylol transfer antibacterial substances, and in particular taurolidine and its analogues, are effective against such toxins not only in the necrotic bone but also in the extracellular fluid of the body, where the toxins are commonly released by both gram-positive and gram-negative bacteria; endotoxins are commonly liberated by gram-negative bacteria on treatment with antibacterial agents, such as antibiotics or povidone-iodine, which cause cell lysis. Gram-positive and gram-negative bacteria are commonly present in the human body even though at levels too low to produce symptoms associated with a disease.

It thus appears that an important feature of the establishment of osteitis or osteomyelitis in bone is the build-up in the bone of toxins from bacteria which may be of exogenous or haematogenous origin which build-up induces necrosis and provides a reservoir of toxic material leading to further necrosis, often over relatively long periods of time.

While the treatment of existing osteitis and osteomyelitis can be greatly improved by the use of such methylol transfer antibacterials, our discovery leads to the possibility of prophylaxis against these diseases by systemic administration of such drugs wherever bone damage is known or suspected. The work of Morrissy referred to above has established that even a cracked bone can provide a nucleus for haematogenous infection of the bone. Thus, if the bacterial toxins can be prevented from gaining a foothold in damaged bone tissue by systemic administration of an effective amount of the methylol transfer agent, osteomyelitis can be avoided.

According to one aspect of the present invention there are provided for prophylaxis against osteitis and osteomyelitis in humans or warm-blooded animals antibacterial methylol transfer compounds of the general formula (I)

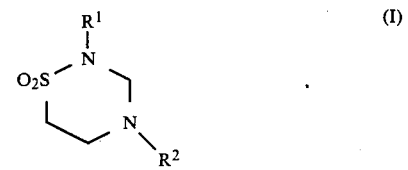

[wherein $R^1$ represents a hydrogen atom or an alkyl group having from 1 to 6 carbon atoms and $R^2$ represents a hydrogen atom, an alkyl group having from 1 to 6 carbon atoms or a group of formula (II)

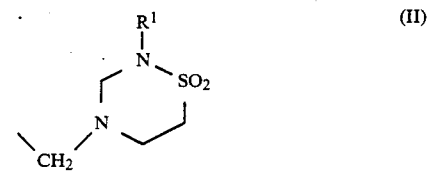

in which $R^1$ is as defined above].

According to another aspect of the invention there is provided a method of prophylaxis of the human or warm-blooded animal body to combat occurrence of osteitis or osteomyelitis, said method comprising administering to a said body wherefor there is a risk of osteitis or osteomyelitis a prophylactically effective amount of a compound of formula (I) as defined above.

Patients considered to be at risk will generally include those suffering from bone injuries, especially those of traumatic origin, including even minor injuries such as cracks.

According to further aspect of the present invention there is provided the use of compounds of formula (I) or pharmaceutical compositions containing as active ingredients compounds of formula (I) for the prophylactic treatment of the human or warm-blooded animal body to combat occurrence of osteitis or osteomyelitis.

According to a yet further aspect of the invention there is provided a pharmaceutical composition for use in the prophylactic treatment of humans or warm-blooded animals to combat occurrence of osteitis or osteomyelitis, said composition comprising an effective amount of a compound of formula (I) together with at least one pharmaceutical carrier or excipient.

In the present invention, of the compounds of formula (I), the compounds taurolidine ($R^1$=H; $R^2$=formula II) and taurultam ($R^1$=$R^2$=H) are particularly preferred.

A particular advantage of the compounds of formula (I) is their very low toxicity; thus methylol transfer activity results in the production of taurine which is found naturally in the body and is particularly non-toxic.

A further advantage of taurolidine is its stability in aqueous solution, enabling the solutions to be pre-packed and stored over relatively long periods. Furthermore, it has recently shown to be non-teratogenic in mice.

The compositions of the invention may be in forms suitable for systemic, e.g. oral or, more particularly, parenteral administration. Oral forms include tablets, capsules, and fluid compositions such as solutions and suspensions. Parenteral forms include sterile aqueous solutions for injection or infusion. Solutions will commonly contain a solubilising agent such as polyvinylpyrrolidone which helps maintain the active substance in solution and also contributes to the isotonicity of the solution.

The polyvinylpyrrolidone (PVP) is preferably incorporated into the solution, e.g. at a concentration in the range 4 to 7% by weight, in order to achieve relatively high concentrations of taurolidine and the relatively insoluble compounds of formula (I). The molecular weight of the PVP should not be greater than 30,000 and is preferably less than 10,000, for example between 200 and 3500. Kollidone 17 (registered Trade Mark) sold by BASF is especially suitable. Such PVP is relatively quickly resorbed and excreted renally.

The daily dose of the active compound depends, in part, on such factors as the body weight of the subject, the extent of the bone injury and any haematogenous infection known to be present but in general will be in the range 10 g to 40 g, more preferably 20 g to 30 g per day. A suitable dosage regime is four 250 ml bottles of a 2% solution of the active compound by i.v. drip infusion with a 4 hour pause or 3 such bottles per day with a 6 hour pause.

The concentration of the substance of formula (I) in such solutions is preferably in the range 0.5 to 5% by weight, depending, at the maximum, on the solubility of the compound. Solutions of 1.0 to 2.0% taurolidine are particularly preferred.

Where the compositions of the invention are in solid form, e.g. as tablets or capsules, they conveniently contain 400 to 700 mg, preferably about 500 mg of the compound of formula (I). As with iv administered solutions, the daily dosage will depend in part upon such factors as the body weight of the subject, the extent of the bone injury and any haematogenous infection known to be present; however oral daily dosages will generally be at least about 10 g, preferably 10 to 30 g.

According to a still further aspect, the present invention provides the use of compounds of formula (I) for the preparation of pharmaceutical compositions for prophylaxis against osteitis or osteomyelitis.

According to a yet further aspect, the invention provides a process for the preparation of a pharmaceutical composition for prophylaxis against osteitis or osteomyelitis, said process comprising admixing a compound of formula (I) together with at least one pharmaceutical carrier or excipient.

The invention also provides one or more compounds of formula (I) as defined above in association with instructions for use in the method of prophylaxis according to the invention.

The following non-limiting Examples are provided to illustrate further the present invention:-

EXAMPLE 1

| Solution | |
| --- | --- |
| Bis-(1,1-dioxo-perhydro-1,2,4-thiadiazin-4-yl)-methane (taurolidine) | 400 g |
| Polyvinylpyrrolidone (Kollidone 17) | 1000 g |
| Sterile water to | 20 liters |

15 Litres double distilled pyrogen free water are filled into a 25 liter glass vessel with stirrer and intensive reflux device and heated to 50° C. with stirring. The taurolidine (400 g) is added followed by PVP (Kollidone 17; 1000 g). After dissolution, the solution is cooled and the pH adjusted to 6.0 with a few drops of 0.1 N hydrochloric acid. The solution is then passed through an adsorption filter to remove microorganisms and pyrogens and through a sterilising millipore filter before being filled into 100 ml vials which are finally autoclaved.

EXAMPLE 2

| Solution | |
| --- | --- |
| Taurultam | 990 g |
| Sterile water ad | 22 liters |

The taurultam is dissolved in the sterile water and filled into sterile bottles, 250 ml in each.

EXAMPLE 3

| Tablet | |
| --- | --- |
| Taurolidine | 500 g |
| Amylum maydis | 60 g |
| Kollidone 25 (polyvinylpyrrolidone) | 50 g |
| Plasdon XL | 20 g |
| Magnesium stearate | 6 g |
| Distilled water | 200 g |

1000 tablets each containing 500 mg taurolidine are produced by conventional means using the above formulation.

In an alternative tablet formulation, the amylum maydis is replaced by 60 g amylum orizae.

EXAMPLE 4

| Solution | |
| --- | --- |
| Taurolidine | 440 g |
| Pharmaceutical gelatin | 88 g |
| Sodium chloride | 99 g |

| Solution | |
|---|---|
| Sterile water to | 22 liters |

The components are dissolved in the sterile water, if necessary using gentle warming and sonication. The solution is then filled into sterile bottles, 500 ml in each.

I claim:

1. A method of treating a human or warm-blooded animal patient suffering from bone injury to prevent the occurrence of osteitis or osteomyelitis, said method comprising administering systemically to said patient a therapeutically effective amount of a compound of formula (I)

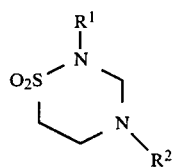

(I)

wherein $R^1$ represents a hydrogen atom or an alkyl group having from 1 to 6 carbon atoms and $R^2$ represents a hydrogen atom, an alkyl group having from 1 to 6 carbon atoms or a group of formula (II)

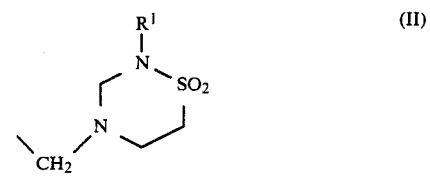

(II)

in which $R^1$ is as defined above.

2. A method as claimed in claim 1 wherein there is administered to said patient a compound of formula (I) selected from the group consisting of taurolidine and taurultam.

3. A method as claimed in claim 1 wherein said compound of formula (I) is administered to said patient intravenously.

4. A method as claimed in claim 3 wherein from 10 to 40 g of said compound of formula (I) is administered daily.

* * * * *